US009757366B2

(12) United States Patent
Mills et al.

(10) Patent No.: US 9,757,366 B2
(45) Date of Patent: Sep. 12, 2017

(54) METHODS FOR THE TREATMENT OF PARKINSON'S DISEASE PSYCHOSIS USING PIMAVANSERIN

(71) Applicant: ACADIA Pharmaceuticals Inc., San Diego, CA (US)

(72) Inventors: Roger Mills, San Diego, CA (US); Hilde Williams, San Diego, CA (US)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 15/246,412

(22) Filed: Aug. 24, 2016

(65) Prior Publication Data
US 2017/0042876 A1 Feb. 16, 2017

Related U.S. Application Data

(63) Continuation of application No. 14/647,438, filed as application No. PCT/US2013/071792 on Nov. 26, 2013, now Pat. No. 9,446,037.

(60) Provisional application No. 61/730,452, filed on Nov. 27, 2012.

(51) Int. Cl.
| A61K 31/445 | (2006.01) |
| A61K 31/4468 | (2006.01) |
| A61K 9/00 | (2006.01) |
| G09B 19/00 | (2006.01) |
| A61K 45/06 | (2006.01) |
| A61K 31/12 | (2006.01) |
| A61K 31/13 | (2006.01) |
| A61K 31/137 | (2006.01) |
| A61K 31/165 | (2006.01) |
| A61K 31/198 | (2006.01) |
| A61K 31/4045 | (2006.01) |
| A61K 31/428 | (2006.01) |
| A61K 31/4453 | (2006.01) |
| A61K 31/46 | (2006.01) |
| A61K 31/473 | (2006.01) |
| G09B 3/06 | (2006.01) |

(52) U.S. Cl.
CPC ........ *A61K 31/4468* (2013.01); *A61K 9/0053* (2013.01); *A61K 31/12* (2013.01); *A61K 31/13* (2013.01); *A61K 31/137* (2013.01); *A61K 31/165* (2013.01); *A61K 31/198* (2013.01); *A61K 31/4045* (2013.01); *A61K 31/428* (2013.01); *A61K 31/4453* (2013.01); *A61K 31/46* (2013.01); *A61K 31/473* (2013.01); *A61K 45/06* (2013.01); *G09B 3/06* (2013.01); *G09B 19/00* (2013.01)

(58) Field of Classification Search
CPC .................................................. A61K 31/455
USPC ....................................................... 514/329
See application file for complete search history.

(56) References Cited

U.S. PATENT DOCUMENTS

| 6,756,393 B2 | 6/2004 | Andersson et al. |
| 6,815,458 B2 | 11/2004 | Andersson et al. |
| 7,601,740 B2 | 10/2009 | Andersson et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,732,615 B2 | 6/2010 | Thygesen et al. |
| 7,790,899 B2 | 9/2010 | Tolf et al. |
| 7,820,695 B2 | 10/2010 | Weiner et al. |
| 7,863,296 B2 | 1/2011 | Weiner et al. |
| 7,868,176 B2 | 1/2011 | Thygesen et al. |
| 7,875,632 B2 | 1/2011 | Weiner et al. |
| 7,923,564 B2 | 4/2011 | Thygesen et al. |
| 7,994,193 B2 | 8/2011 | Weiner et al. |
| 8,008,323 B2 | 8/2011 | Weiner et al. |
| 8,227,487 B2 | 7/2012 | Weiner et al. |
| 8,236,960 B2 | 8/2012 | Thygesen et al. |
| 8,377,959 B2 | 2/2013 | Weiner et al. |
| 8,618,130 B2 | 12/2013 | Weiner et al. |
| 8,921,393 B2 | 12/2014 | Weiner et al. |
| 9,050,343 B2 | 6/2015 | Peters et al. |
| 9,211,289 B2 | 12/2015 | Weiner et al. |
| 9,296,694 B2 | 3/2016 | Andersson et al. |
| 2014/0329903 A1 | 11/2014 | Burstein et al. |

FOREIGN PATENT DOCUMENTS

| WO | 2004064738 A1 | 5/2004 |
| WO | 2008144665 A1 | 11/2008 |
| WO | 2014085362 A1 | 5/2014 |

OTHER PUBLICATIONS

Aarsland et al., "Decreased burden among caregivers of patients with Parkinson's disease psychosis (PDP) treated with pimavanserin, a selective 5-HT2A inverse agonist," (Meeting Abstract) Neurology, 2015, vol. 84, No. 14 Supplement P6.044.

Norton et al., "Caregivers of PDP patients have an increased risk of developing emotional and social distress that is decreased when PDP is treated with pimavanserin," (Meeting Abstract) Journal of Parkinson's Disease, Sep. 2016, vol. 6, No. s1, p. 257, Abstract No. P42.11.

Norton et al., "Decreased burden among caregivers of patients with Parkinson's disease psychosis (PDP) treated with pimavanserin, a selective 5-HT2A inverse agonist," (Meeting Abstract) Journal of Parkinson's Disease, Sep. 2016, vol. 6, No. s1, p. 88, Abstract No. P12.08.

Friedman et al., "A Multi-Center, Placebo-Controlled, Double-Blind Trial to Examine the Safety and Efficacy of Pimavanserin in the Treatment of Psychosis in Parkinson's Disease," Neurology, (Mar. 2010), p. A299, vol. 74, No. 9, Suppl. 2.

Abbas et al., "Pimavanserin tartrate: a 5-HT2A inverse agonist with potential for treating various neuropsychiatric disorders," Expert Opinion on Pharmacotherapy, (Dec. 2008) pp. 3251-3259, vol. 9, No. 18.

(Continued)

*Primary Examiner* — Raymond Henley, III
(74) *Attorney, Agent, or Firm* — Jones Day

(57) ABSTRACT

Methods for the treatment of Parkinson's disease psychosis which comprise the administration of pimavanserin.

6 Claims, 4 Drawing Sheets

(56) References Cited

OTHER PUBLICATIONS

"ACP-103," Drugs of the Future, Prous Science, ES, (Jan. 2006), pp. 939-943, vol. 31, No. 11.
International Searching Authority, "International Search Report for International Application No. PCT/US2013/071792," (mailed Jan. 1, 2014), 4 pages.
Meltzer et al., "Co-therapy with pimavanserin and risperidone 2 mg provides an improved clinical profile," Schizophrenia Research, (Jan. 16, 2008), p. 16, vol. 98, Elsevier, Netherlands.
Meltzer et al., "Pimavanserin, a Serotonin(2A) Receptor Inverse Agonist, for the Treatment of Parkinson's Disease Psychosis," Neuropsychopharmacology, (Mar. 2010), pp. 881-892, vol. 35, No. 4.

METHODS FOR THE TREATMENT OF PARKINSON'S DISEASE PSYCHOSIS USING PIMAVANSERIN

CROSS REFERENCE TO RELATED APPLICATIONS

This application is a continuation of U.S. application Ser. No. 14/647,438, filed May 26, 2015, now U.S. Pat. No. 9,446,037, which is a U.S. National Stage filing under 35 U.S.C. §371 of International Application No. PCT/US2013/071792, filed Nov. 26, 2013, which claims priority to U.S. Provisional Application No. 61/730,452, filed Nov. 27, 2012; the contents of each of which are incorporated herein by reference in their entireties.

FIELD

Provided herein are methods for the treatment of Parkinson's disease psychosis (hereafter, "PDP") which comprise the administration of pimavanserin.

BACKGROUND

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, Rev. Neurol. 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, Biology of Serotonergic Transmission, 1982; Boullin, Serotonin In Mental Abnormalities 1:316 (1978); Barchas, et al., Serotonin and Behavior, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., The Peripheral Actions of 5-Hydroxytryptamine, 246 (1989); Saxena, et al., J. Cardiovascular Pharmacol. 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, Neuropsychopharmacology, 21:106S-115S (1999); Barnes & Sharp, Neuropharmacology, 38:1083-1152 (1999); Glennon, Neurosci. Biobehavioral Rev., 14:35 (1990)).

Given the broad distribution of serotonin within the body and its role in a wide range of physiological and pathological processes, it is understandable that there is tremendous interest in drugs that affect serotonergic systems (Gershon, et al., The Peripheral Actions of 5-Hydroxytryptamine, 246 (1989); Saxena, et al., J. Cardiovascular Pharmacol. 15: Supp. 7 (1990)).

The effects of serotonin are mediated by at least 15 genetically distinct 5-HT receptor subtypes have been identified and assigned to one of seven families (5-HT1-7). Each subtype displays a unique distribution, preference for various ligands, and functional correlate(s). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis. Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Parkinson's disease is a common neurodegenerative disease which affects a significant part of the elderly population. PDP is a particularly devastating neuropsychiatric complication of Parkinson's disease that affects a majority of the patient population with advanced disease. Current treatment primarily involves pharmacotherapy with a class of drugs known as antipsychotics. Antipsychotics have been shown to effective in ameliorating positive symptoms in PDP (e.g., hallucinations and delusions), yet they frequently do not improve negative symptoms (e.g., social and emotional withdrawal, apathy, and poverty of speech).

Currently, antipsychotics are prescribed to treat psychotic symptoms in PDP patients but the use of these compounds is limited by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of some of these adverse effects. However, atypical agents also have the potential for serious side effects including increased risk of stroke, abnormal shifts in sleep patterns, extreme tiredness and weakness, metabolic disorders (including hyperglycemia and diabetes), and weight gain. One of the most common reasons for noncompliance and discontinued use of antipsychotic medication is weight gain. Non-compliance can lead to increased hospitalization and health care costs.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects as well as some additional undesired effects of antipsychotic therapies such as a worsening of depression symptoms, anhedonia and impairment of cognitive processes. Antagonism of 5-HT2A receptors is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects or other undesired effects associated with blockade of dopamine $D_2$ receptors.

Traditionally, GPCRS such as the 5-HT2A receptor have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

SUMMARY

Provided herein are methods for the treatment of Parkinson's disease psychosis (hereafter, "PDP") which comprise the administration of pimavanserin. Also provided herein are methods of treating Parkinson's disease psychosis in a patient as described above, wherein pimavanserin is administered in alternation or in combination with an anti-Parkinson's agent.

Another embodiment described herein includes a method of inducing early or rapid onset of an antipsychotic effect, comprising administering pimavanserin to a subject suffering from PDP.

Also provided herein are methods for the improvement of sleep in a Parkinson's disease patient, comprising the oral administration of pimavanserin, or a pharmaceutically acceptable salt thereof. In one embodiment, the improvement of sleep is measured on the Scales for Outcomes in Parkinson's Disease-Sleep scale.

Also provided herein is a method for reducing caregiver burden during the treatment of Parkinson's disease psychosis by the administration of pimavanserin to a PDP patient.

Also provided herein is a method for excluding from a clinical study Parkinson's disease psychosis patients with a high likelihood for placebo response, the method comprising screening a group of Parkinson's disease psychosis patients by administering one day to two weeks of social interaction therapy designed for Parkinson's disease psychosis patients, wherein patients who respond sufficiently to the social interaction therapy are excluded from a subsequent clinical study.

DETAILED DESCRIPTION

Figure 1:
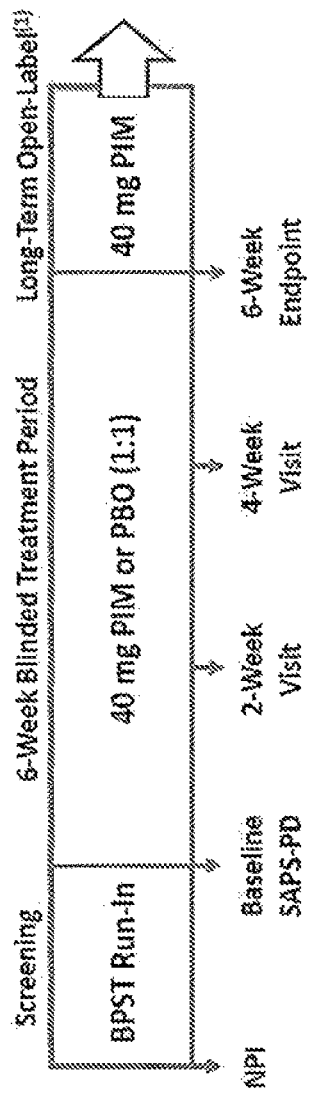
FIG. 1 depicts the PDP patient pathway from screening to open-label treatment in the Phase III clinical trial.
Figure 2:
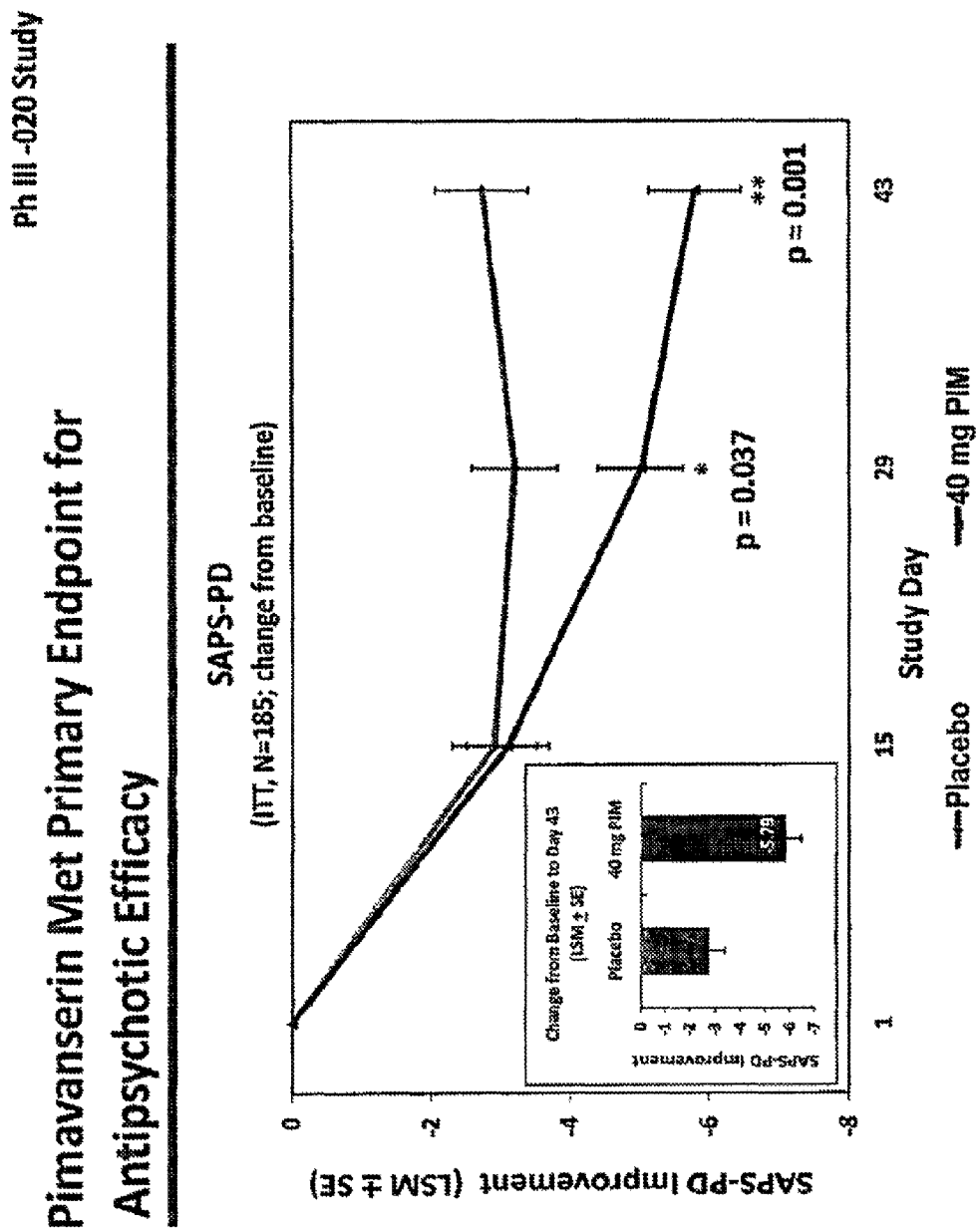
FIG. 2 is a graph depicting antipsychotic efficacy of pimavanserin in PDP patients on the Scale for the Assessment of Positive Symptoms (SAPS-PD).
Figure 3:
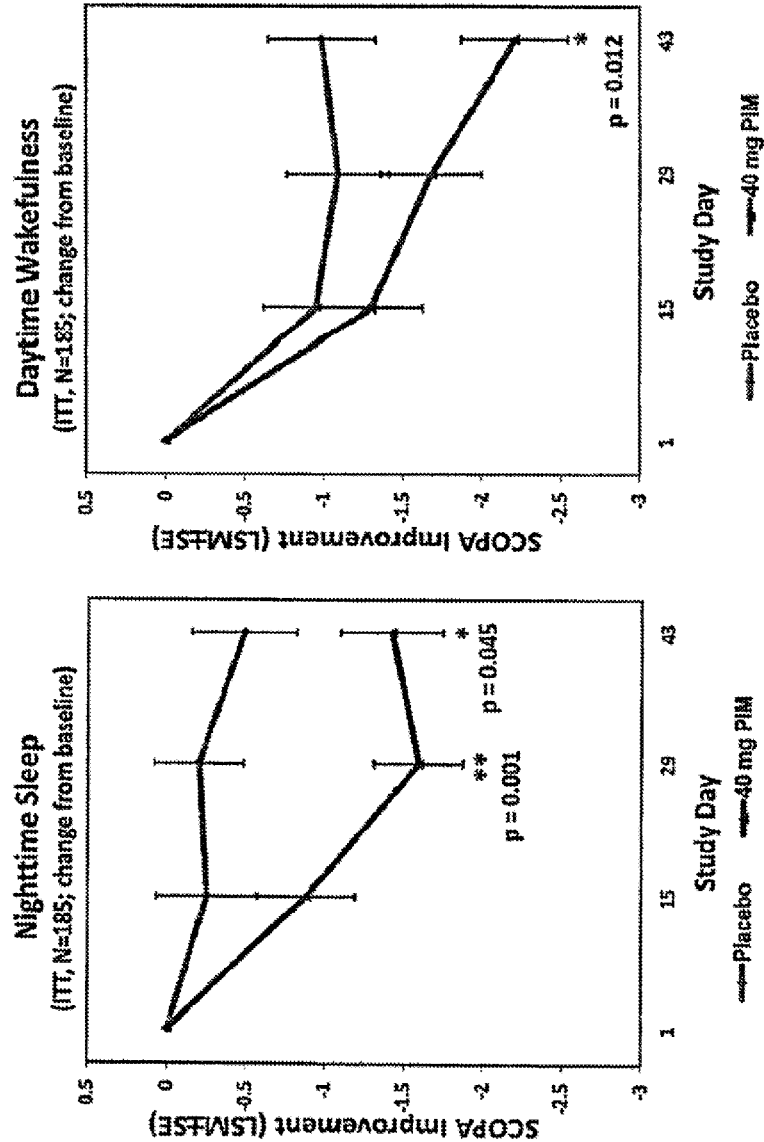
FIG. 3 is a graph depicting improvement in nighttime sleep and daytime wakefulness of PDP patients treated with pimavanserin.
Figure 4:
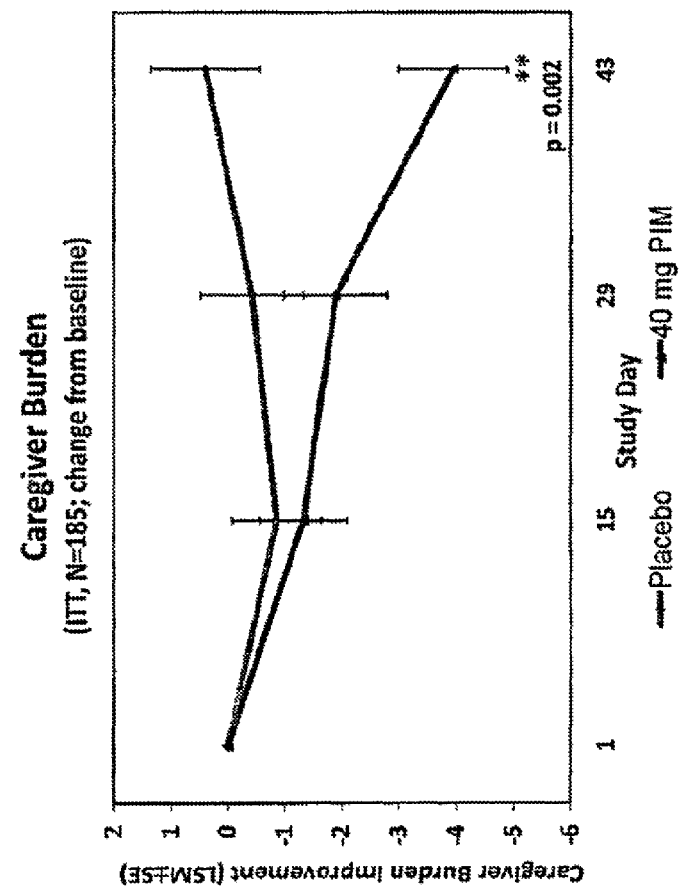
FIG. 4 is a graph depicting reduction in caregiver burden as a result of treatment of PDP patients with pimavanserin.

Provided herein are methods for the treatment of Parkinson's disease psychosis which comprise the administration of pimavanserin. Also provided herein are methods of treating Parkinson's disease psychosis in a patient as described above, wherein pimavanserin is administered in alternation or in combination with an anti-Parkinson's agent.

Another embodiment described herein includes a method of inducing a rapid or early onset of an antipsychotic effect in a patient suffering from PDP, comprising administering pimavanserin to a subject suffering from PDP such that there is a rapid or early onset of an antipsychotic effect. Rapid or early onset of an antipsychotic effect is measured as compared to conventional therapies for PDP, such as the administration of an antipsychotic agent. Exemplary agents used for the treatment of PDP include, but are not limited to, clozapine, olanzapine, aripiprazole, ziprasidone, quetiapine, cholinesterase inhibitors, tacrine, donepezil, and rivastigmine.

In some embodiments, administration of pimavanserin results in an early onset of one or more efficacious effects. In some embodiments, the efficacious effect is the reduction of psychotic symptoms. In one embodiment, the efficacious effect is measured by the Scale for the Assessment of Positive Symptoms (SAPS). SAPS is published by The Movement Disorder Society at www.movementdisorders.org (last visited Nov. 13, 2012); see also Fernandez et al., *Movement Disorders,* 2008, 23(4): 484-500.

In one embodiment, the efficacious effect is measured by the combined score for the modified 9-item Hallucinations and Delusions domains of the Scale for the Assessment of Positive Symptoms for Parkinson's disease psychosis (SAPS-PD). See Voss et al., *Parkinsonism & Relat. Disord.,* 2013, 19(3): 295-99 (e-publication was available on Dec. 1, 2012 at http://www.ncbi.nlm.nih.gov/pubmed/23211417). The SAPS-PD scale is designed to enhance sensitivity for assessing PDP and reduce noise or the placebo effect in clinical trials.

SAPS-PD includes the following 9 items from the hallucinations and delusions SAPS scale: auditory hallucinations, voices conversing, somatic or tactile hallucinations, visual hallucinations, global rating of severity of hallucinations, persecutory delusions, delusions of jealousy, delusions of reference, and global rating of severity of delusions. Each item is assessed according to standard SAPS methodology. See Fernandez et al., *Movement Disorders,* 2008, 23(4): 484-500.

In another embodiment, the efficacious effect is measured by changes in the Clinical Global Impression Scale (CGI), with emphasis on severity (CGI-S) and improvement (CGI I) of psychosis. See Busner & Targum, *Psychiatry,* 2007, vol. 4(7): 28-37.

All combinations of the above measurements of efficacy are part of the disclosure provided herein.

In some embodiments, the early or rapid onset of efficacious activity is demonstrated by a clinically relevant therapeutic effect being achieved greater than about 10%, 20%, 30%, 40%, 50%, 60%, 70%, 80%, 90%, 100%, 110%, 130%, 150%, 200%, 300%, 400%, or 500% faster than when pimavanserin is administered alone at an efficacious dose. In some embodiments, the early or rapid onset of efficacious activity is demonstrated by a greater percentage of patients experiencing an efficacious effect after a specified period of time as compared to placebo or lack of treatment. In various embodiments, the percentage of patients experiencing an efficacious effect is increased by greater than about 20%, 30%, 40%, 50%, 60%, 70%, 80%, 90%, 100%, 110%, 130%, 150%, 200%, 300%, 400%, or 500%. In some embodiments, the specified period of time is two weeks, four weeks or six weeks. In one embodiment, the specified period of time is six weeks.

Also provided herein is a method for the improvement of sleep in a Parkinson's disease patient, comprising the oral administration of pimavanserin, or a pharmaceutically acceptable salt thereof. In one embodiment, the improvement of sleep is measured on the Scales for Outcomes in Parkinson's Disease-Sleep scale. See Martinez-Martin et al. *Movement Disorders,* 2008, vol. 23(12): 1681-1688; Marinus et al., *SLEEP,* 2003, vol. 26(8): 1049-54.

In one embodiment, provided herein is a method for the improvement of sleep in a Parkinson's disease patient, comprising the oral administration of pimavanserin, or a pharmaceutically acceptable salt thereof, to the patient in a daily dose of about 40 mg, wherein the improvement of sleep is measured on the Scales for Outcomes in Parkinson's Disease-sleep scale (SCOPA-sleep). In one embodiment, the method is for the improvement of nighttime sleep as measured or determined by the SCOPA-sleep scale (nighttime sleep problems). In another embodiment, the method is for the improvement of daytime wakefulness as measured or determined by the SCOPA-sleep scale (daytime sleepiness).

Other scales may be used to evaluate nighttime sleep and daytime wakefulness, as described in Marinus et al., *SLEEP,* 2003, vol. 26(8): 1049-54.

Also provided herein is a method for reducing caregiver burden during the treatment of Parkinson's disease psychosis by the administration of pimavanserin to a PDP patient. In some embodiments, the reduction in caregiver burden is measured on the Caregiver Burden Scale. In one embodiment, provided herein is a method for reducing caregiver burden during the treatment of Parkinson's disease psychosis, comprising the oral administration of pimavanserin, or a pharmaceutically acceptable salt thereof, to a Parkinson's disease patient in a daily dose of about 40 mg, wherein the reduction in caregiver burden is measured on the Caregiver Burden Scale. See Zarit et al, 1980, *The Gerontologist,* vol. 20: 649-655. The Caregiver Burden Scale is completed by the subject's attending caregiver. It allows assessment of the potential for pimavanserin to ameliorate the stress on caregivers. This self-administered 22-item questionnaire is commonly used in caregivers of the dementia patient population, most specifically in caregivers of subjects with Alzheimer's disease. Nonetheless, it has been reported to have high reliability in PD. See Aarsland et al., *J. Neurol. Neurosurg. Psychiatry,* 1999, vol. 67(4): 492-496.

Also provided herein are methods of treating Parkinson's disease psychosis in a patient as described above, wherein pimavanserin is administered in alternation or in combination with an anti-Parkinson's agent. In some embodiments, the patient is concurrently treated with an anti-Parkinson's agent. In some embodiments, the anti-Parkinson's agent is selected from the group consisting of levodopa, carbidopa, carbidopa-levodopa, benserazide-levodopa, benztropine, trihexylphenidyl, amantadine, pramipexole, selegiline, rasagiline, entacapone, tolcapone, ropinirole, and apomorphine.

Also provided herein is a method for excluding from a clinical study Parkinson's disease psychosis patients with a high likelihood for placebo response, the method comprising screening a group of Parkinson's disease psychosis patients by administering one day to two weeks of social interaction therapy designed for Parkinson's disease psychosis patients, wherein patients who respond sufficiently to the social interaction therapy are excluded from a subsequent clinical study.

In some embodiments, the social interaction therapy designed for Parkinson's disease psychosis patients is a brief psycho-social therapy (BPST) designed as per current supportive care guidelines and modified for PD (BPST-PD). Patients who responded sufficiently to this non-pharmacologic social interaction therapy (i.e., who no longer meet study entry criteria) are excluded from the clinical study, whereas patients who do not materially improve during this phase have the option of entering the treatment period of the clinical study early.

In some embodiments, BPST-PD used is as described in Example 7, infra.

Also provided herein is a method for conducting a clinical study in a group of Parkinson's disease psychosis patients, the method comprising:
  (i) screening a group of Parkinson's disease psychosis patients by administering one day to two weeks of social interaction therapy designed for Parkinson's disease psychosis patients, wherein patients who respond to the social interaction therapy are excluded from the clinical study;
  (ii) dividing the patients who were not excluded into a treatment group and a placebo group;

(iii) administering a drug to the treatment group for a designated period of time; and (iv) evaluating the results of the clinical study by comparing the treatment group to the placebo group.

In one embodiment, pimavanserin is administered to the patients in the treatment group.

Compound

Pimavanserin, which is also known as N-(1-methylpiperidin-4-yl)-N-(4-fluorophenylmethyl)-N'-(4-(2-methylpropyloxy)phenylmethyl)carbamide, N-[(4-fluorophenyl)methyl]-N-(1-methyl-4-piperidinyl)-N'-[[4-(2-methylpropoxy)phenyl]methyl]-urea, 1-(4-fluorobenzyl)-1-(1-methylpiperidin-4-yl)-3-[4-(2-methylpropoxy)benzyl]urea, or ACP-103 has the structure of Formula (I):

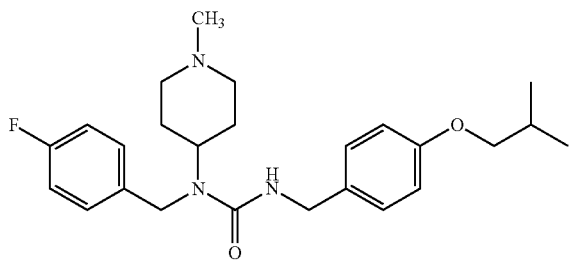

Pimavanserin and methods for its use are described in U.S. Pat. Nos. 7,601,740; 7,659,285; 7,713,995; 7,732,462; 7,994,193 and 8,008,323, the entirety of each of which is hereby incorporated by reference. Pimavanserin can be obtained in a number of salt and crystalline forms. Exemplary pharmaceutically acceptable salts include the tartrate, hemi-tartrate, citrate, fumarate, maleate, malate, phosphate, succinate, sulphate, and edisylate (ethanedisulfonate) salts. Pimavanserin salts including the aforementioned ions, among others, are described in U.S. Patent Publication No. 2006-0111399, filed Sep. 26, 2005, the entirety of which is incorporated herein by reference. In an embodiment provided herein, pimavanserin is the tartrate salt of pimavanserin. Several crystalline forms of the tartrate salt of pimavanserin have been described in U.S. Patent Publication No. 2006-0106063, filed Sep. 26, 2006, the entirety of which is incorporated herein by reference. See also U.S. Pat. Nos. 7,732,615; 7,795,547; 7,790,899; 7,868,176, the entirety of each of which is incorporated herein by reference. In an embodiment provided herein, pimavanserin is the crystalline form of the tartrate salt of pimavanserin Form A. In another embodiment, pimavanserin is the crystalline form of the tartrate salt of pimavanserin Form C. Pimavanserin (including, for example, the tartrate salt) may be formulated into tablets, such as is described in U.S. Patent Publication Nos. 2007-0260064, filed May 15, 2007 and 2007-0264330, filed May 15, 2007, each of which are incorporated herein by reference in their entireties. Metabolites of pimavanserin are described in U.S. Patent Publication No. 2009/0082342, the entirety of which is hereby incorporated by reference.

The pharmacological activity of pimavanserin has been previously reported. See U.S. Patent Publication Nos. 2004/0213816 and 2009/0053329, the entirety of each of which is hereby incorporated by reference. Pimavanserin is active in a number of models thought to be predictive of antipsychotic activity such as DOI ((±)-2,5-dimethoxy-4-iodoamphetamine, a serotonin agonist) induced head twitches in the rat and attenuation of hyperactivity in mice induced by the N-methyl-D-aspartate antagonist MK-801. The compound was effective in these models at oral doses of 3 and 10 mg/kg. In a rat model of deficits in sensory motor gating similar to those exhibited by schizophrenics, pimavanserin at doses of 1 and 3 mg/kg SC potently reversed the gating deficit induced by DOI. Pimavanserin also failed to disrupt learning of a simple auto-shaped response in mice at intraperitoneal doses up to 32 mg/kg. The pharmacological profile of pimavanserin suggests it will be effective as an antipsychotic agent without the side effects common to other compounds in this class. Thus, pimavanserin will have antipsychotic activity when used to treat schizophrenic subjects.

Definitions

The term "pharmaceutically acceptable salt" refers to a salt of a compound that does not cause significant irritation to an organism, such as a human, to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The terms "improvement," "improved" and "improves" as used herein with respect to the clinical setting refer to a clinically relevant effect being achieved greater than about 5%, 10%, 20%, 30%, 40%, 50%, 60%, 70%, 80%, 90%, 100%, 110%, 120%, 130%, 140%, 150%, 160%, 170%, 180%, 200%, 300%, 400%, or 500% when compared to baseline after a specified period of time. In some embodiments, the improvement refers to improved efficacious effect in a single patient after the administration of pimavanserin as compared to baseline (i.e., prior to the administration of pimavanserin). In other embodiments, the improvement refers to the demonstration of efficacy by a greater percentage of patients experiencing an efficacious effect after a specified period of time as compared to placebo or lack of treatment. In various embodiments, the percentage of patients experiencing an efficacious effect is increased by greater than about 5%, 10%, 20%, 30%, 40%, 50%, 60%, 70%, 80%, 90%, 100%, 110%, 120%, 130%, 140%, 150%, 160%, 170%, 180%, 200%, 300%, 400%, or 500% when compared to placebo or lack of treatment. In some embodiments, the specified period of time is about two weeks, four weeks or six weeks. In one embodiment, the specified period of time is six weeks.

The term "nighttime sleep" refers to sleep at night. Improvement of nighttime sleep refers to improvement of patient problems with sleeping at night, including but not limited to the ability to fall asleep and the ability to sleep through the night without waking. Improvement of nighttime sleep may be measured or determined by use of the SCOPA-sleep scale (nighttime sleep problems). Other scales may be used to evaluate nighttime sleep, as described in Marinus et al., *SLEEP*, 2003, vol. 26(8): 1049-54.

The term "daytime wakefulness" refers to the ability to remain awake during daylight hours. Improvement of daytime wakefulness refers to reduced episodes of dozing off and improvement in the ability to stay awake during daylight hours. Improvement of daytime wakefulness may be measured or determined by use of the SCOPA-sleep scale (daytime sleepiness). Other scales may be used to evaluate daytime wakefulness, as described in Marinus et al., *SLEEP*, 2003, vol. 26(8): 1049-54.

Pharmaceutical Compositions

Techniques for formulation and administration of the compositions described herein may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation.

Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

EXAMPLES

Example 1: Preparation of Pimavanserin

Pimavanserin may be synthesized by methods described below, or by modification of these methods. Ways of modifying the methodology include, among others, modification in temperature, solvent, reagents, etc. An exemplary method of preparing pimavanserin is as follows.

a) Preparation of

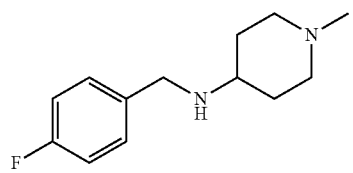 [SMILES: CN1CCC(NCc2ccc(F)cc2)CC1]

The reaction step was performed in three batches, which were each manufactured on the same scale as described below and the resulting products combined for further use in the next step.

N-Methylpiperidone (33.0 kg) and 4-fluorobenzylamine (35.4 kg) were dissolved in methanol (220.1 kg) at 15-19° C. (exothermic dissolution), and a suspension of 5% palladium on charcoal (1.2 kg) in methanol (16.8 kg) was added under nitrogen and the line rinsed with methanol (5.6 kg). The bulk was heated to 23-27° C. and hydrogenated at the same temperature and ~5 bar until the hydrogen absorption stopped (~12 h). The residual starting material was checked by GC, and the bulk was clarified on a Lens filter equipped with a thin Celtrox pad and 2×G92 filter papers. The line was rinsed with methanol (9.8 kg). The solvent was distilled under reduced pressure (265-60 mbar; 35-40° C.) and the oily residue was purified by fractional distillation under vacuum at ~135-140° C. at 8-0.5 mbar. Impure fractions of the three batches were combined and redistilled.

Total yield (combined three batches and redistilled fractions): 147.4 kg (78.1%).

b) Preparation of

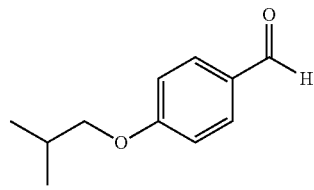

The reaction step was performed in two batches. 4-Hydroxybenzaldehyde (141 kg) was dissolved in dimethylformamide (335 kg) at 15-25° C., then solid potassium carbonate (323 kg) and potassium iodide (19 kg) were added portion wise at <30° C. and the suspension was heated up to 78-82° C. The temperature of the condenser was fixed to −10° C. and isobutylbromide (317 kg) was added to the suspension over 4 h 50 min at 78-82° C. At the end of the addition, the mixture was stirred for 2 h at 78-82° C. and residual starting material was checked by HPLC. The suspension was cooled to 20-30° C., diluted with 100% ethanol (501 kg, denatured with isopropanol), stirred for 15 min at 20-30° C. and centrifuged (3 loadings) to remove the excess of carbonate and potassium bromide. The line and the cake were washed with 100% ethanol (2×32 kg/loading). The solution is used as such in the next step.

c) Preparation of

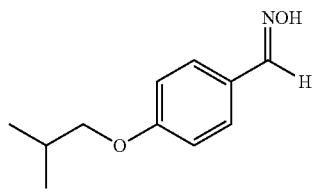

To the aldehyde solution resulting from Step b, 50% hydroxylamine in water (115 kg) was added at room temperature over ~0.5 h (the addition is slightly exothermic), the line washed with ethanol (8 kg), then the bulk was heated up to 73-77° C. and stirred at this temperature for 2 h. The bulk was concentrated under reduced pressure (250-120 mbar, 45-55° C.) to ~850 L, the residue quenched with water (951 kg) at 45-55° C. and the residual ethanol distilled under vacuum (270-150 mbar, 45-55° C., residual volume=1466 L). The bulk was diluted with petrol ether 60-90 (557 kg) and heated at reflux (~60° C.) to reach complete dissolution (~20 min, visual check). The solution was cooled down to 8-12° C. (crystallization occurs at T=~27° C.) over ~5.5 h. After 0.5 h stirring at 10° C., the mixture was cooled to 0-5° C. and stirred at this temperature for 2 h. The bulk was centrifuged (3 loadings) and the cake washed with petrol ether (2×23 kg/loading), then dried under reduced pressure at 40° C. to afford the crude oxime (212 kg).

Recrystallization:

The crude product (212 kg) was dissolved in hexane (642 kg) at 15-25° C. and the suspension heated up to ~62° C. Charcoal (6 kg) in hexane (26 kg) was added and the suspension was stirred for 0.5 h. After filtration (the filter was washed with 33 kg hexane), the solution was cooled to crystallisation temperature (~55° C.), and the mixture was stirred for 1 h at this temperature. The suspension was cooled to 10-15° C. After stirring for ~2 h at that temperature, the bulk was centrifuged (3 loadings) and the cake washed with cold hexane (2×13 kg/loading), then dried under reduced pressure at 40° C.

Yield oxime: 196 kg (87.9% over the two steps)

d) Preparation of

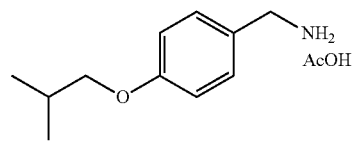

The oxime (198 kg) from Step c was dissolved in ethanol (1148 kg, denatured with isopropanol). Raney nickel catalyst (29 kg) was washed with ethanol (692 kg) until the water content by Karl Fischer was below 300 ppm, then the anhydrous Raney-Nickel was added under nitrogen to the oxime solution, the line washed with ethanol (62 kg) and the suspension cooled down to −10° C. Ammonia gas (229 kg) was added under vacuum over ~6 h (the addition is exothermic). Then the suspension was heated to 49° C. The internal pressure increased to ~3 bar. The bulk was hydrogenated at 49° C. and 4 bar until the hydrogen absorption stopped (~9 h) and the end of reaction was checked by HPLC. The suspension was cooled to 13° C., the excess of ammonia was removed, and the bulk clarified by filtration over Celtrox (4 kg). The line was washed with ethanol (317 kg). The solvent was distilled under reduced pressure (150-10 mbar, 40-50° C.) and the residue dissolved in toluene (780 kg) at ~40° C. The solution was transferred to a new reactor (previous reactor washed with 57 kg toluene), and cooled to 22° C. Acetic acid (60 kg) was slowly added (exothermic reaction) at 22° C. and the bulk heated during 20 min to ~95° C. until complete dissolution was reached. The solution was cooled rapidly to 80° C. and seeded with amino acetate product (50 g). The suspension was stirred at the crystallization temperature for 30 min, cooled to 10° C. and stirred for ~1 h at this temperature. The bulk was centrifuged (3 loadings) and the cake washed with cold toluene (2×48 L/loading) and finally dried under vacuum at (9-16 mbar) at ~50° C. for 28 h.

Yield: 207 kg (83.6%)

e) Preparation of

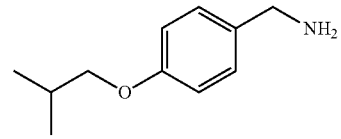

A solution of the aminoacetate (269 kg) from Step d in water (431 kg) was basified with 30% sodium hydroxide solution (305 kg) to pH 14 at 20-25° C. Then the amino base product was extracted with toluene (933 kg) at 43-47° C. by stirring for 15 min. The bulk was decanted during 15 min at 43-47° C.; if necessary the pH was adjusted to >12 with additional 30% NaOH, then the layers were separated. The organic layer was washed with water (359 kg), then concentrated under vacuum (200-20 mbar) at 45-50° C. to give the aminobase as an oily residue.

f) Preparation of

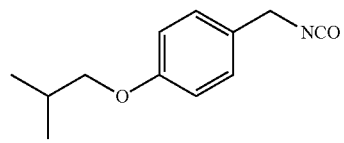

The aminobase from Step e was dissolved at 48° C. in toluene (825 kg) and the water content of the solution checked (KF<300 ppm). The toluene solution was cooled to 1-5° C. and hydrogen chloride (gas, 45.1 kg) was slowly introduced during ~3 h through a canula at $T_{max}$=10° C. (gas introduction is very exothermic). At the end of the addition, the bulk was heated up to 97-103° C. and phosgene (166 kg) was slowly introduced (~4 h) through a canula. At the end of the addition, the bulk was cooled down to 80-84° C. and the reaction was checked by TLC. Additional phosgene (16 kg) was introduced at 100° C., upon which the bulk turned to a clear solution. After further stirring of the mixture 1 h at 100° C., the bulk was cooled to 80-84° C. The solution was concentrated under vacuum (250-50 mbar) at the same temperature to 770 L. The bulk was checked for the absence of residual phosgene and the crude isocyanate solution in toluene was cooled to 20-25° C., filtered through a cartridge filter 0.3 micron.

Yield: Toluene solution of the isocyanate: 687 kg (34.7% a/a of product by GC), 234.4 kg product (100%, over Steps e and f).

g) Preparation of the Title Compound

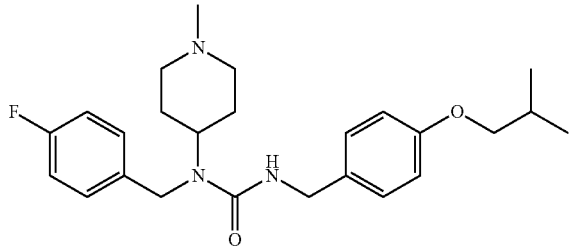 [SMILES: CC(C)COc1ccc(CNC(=O)N(Cc2ccc(F)cc2)C2CCN(C)CC2)cc1]

A solution of the isocyanate from Step f in toluene (301 kg, ~34%) was added in 30 min to a solution of the fluoramine (109 kg) from Step a in tetrahydrofuran (948 kg) at 40° C. and the line washed with tetrahydrofuran (48 kg). The mixture was stirred for ~3 h until complete dissolution. Residual fluoramine was checked by TLC, and an additional amount of the isocyanate solution (6 kg, ~34% in toluene) was added and the mixture stirred for 1 h at 40° C. and checked again by TLC. The solvent was removed by distillation under reduced pressure (300-20 mbar) at Tjacket=50° C. Ethanol (663 kg) was added to the residue at 25° C. and the mixture heated to 40-45° C. over 2.5 h and stirred at this temperature for ~2 h until complete dissolution.

Example 2—Preparation of Pimavanserin Hemi-Tartrate

A previously prepared solution of tartaric acid (41 kg) in ethanol (480 kg) at 43° C. was added at 43° C. over 40 min to the ethanol solution produced in Example 1(g) and the line washed with 16 kg ethanol. The solution was cooled to 37° C. and seeded with pimavanserin Form C (0.5 kg) and the product crystallized at ~34° C. The suspension was stirred at this temperature for 30 min then cooled to 2° C. over 2.5 h and stirred for 2.5 h more at this temperature. The product was centrifuged (2 loadings) and the cake was washed with ethanol (3×15 kg/loading). The obtained crude product was dried under vacuum (50 to 5 mbar) at 45° C. for about 49 h 20 min, sieved at 3 mm, and dried for another 5 h under vacuum. Yield of crude: 214 kg (86.0%).

Example 3—Preparation of Crystalline Form A of Pimavanserin Hemi-Tartrate

The crude tartrate (212 kg) salt from Example 2 was heated in ethanol (948 kg) at 73-75° C. (reflux) for ~1 h until dissolution. The hot mixture was filtered through a 0.3 μm cartridge filter, the line washed with ethanol (30 kg) and the bulk heated to reflux for ~0.5 h. The solution was cooled over ~1 h to 49° C. and seeded with pimavanserin (0.4 kg) and the product crystallized at 48° C. The suspension was stirred at this temperature for 30 min. The suspension was then cooled to −10° C. over ~8 h and stirred at this temperature for an additional 8 h. The product was centrifuged (2 loadings) and the cake washed with cold ethanol (3×21 kg/loading). The wet product was dried under vacuum (50 to 5 mbar) at 45° C. for 40.5 h. The resulting product was reworked according to the procedure described below. Yield: 189 kg (89.2%) Rework:

Step #1: Free Basing of the Tartrate to Isolate Urea as a Solid

NaOH 30% (50 kg) was added over ~15 min to a suspension of water (378 kg), toluene (983 kg) and the tartrate salt (189 kg). The mixture was heated and stirred at 38° C. for 45 min, additional NaOH 30% (6 kg) was added for the pH to reach 12-14. The mixture was stirred at 38° C. for 30 min until complete dissolution and the pH checked. Then, the reaction mixture was settled at 38° C., the layers were separated and the aqueous layer was discarded. The organic layer was washed with water (378 kg) at 38° C. and the toluene distilled at 45-50° C. under vacuum (200-80 mbar) to ~380 L. Heptane (776 kg) was added to the distillation residue at 48° C. to crystallize the urea. The suspension was stirred at 50° C. for 30 min, then cooled to 1° C. over ~3 h and stirred at this temperature for 1 h. The product was centrifuged (2 loadings) and the cake washed with cold heptane (2×27 kg/loading). The wet product (urea) was dried under vacuum (40 to 1 mbar) at 50° C. for about 12 h and sieved at 2 mm. Yield: 147 kg (91.5%)

Step #2: Re-Formation of the Tartrate by Addition of Tartaric Acid

The urea (147 kg) in ethanol (535 kg) was stirred at 40-45° C. until complete dissolution, the solution filtered over a 0.3 μm cartridge and the line washed with ethanol (59 kg). A solution of tartaric acid (26.3 kg) in ethanol (223 kg) was added over 40 min through a 0.3 μm cartridge to the solution of the urea (147 kg, from Step #1) in ethanol (594 kg) at 40-45° C., and the line and reactor washed with ethanol (19 kg). The product crystallized during the introduction. The suspension was stirred at 43° C. for 30 min then cooled to −5° C. over ~6 h and stirred at this temperature for 2 h. The product was centrifuged (3 loadings) and the cake washed with cold ethanol (2×19 kg/loading). The wet product was dried under vacuum (40-7 mbar) at 45° C. for about 34 h, sieved at 3 mm, and drying continued (20-7 mbar, 45° C.) for additional 6 h to produce dry crystalline Form A. Yield: 167 kg (96.8%).

Example 4—Preparation of Crystalline Form C of Pimavanserin Hemi-Tartrate

A suspension of crystalline Form A (167 kg) from Example 3 in pre-filtered and degassed methylethylketone (942 kg) was heated to 60° C. and stirred at this temperature for ~2 h. The suspension was seeded with a suspension of crystalline Form C (5.6 kg) in methylethylketone (41 kg, filtered and degassed) and stirred at 60° C. for another 12 h. A sample was taken to check the complete conversion into Form C. The mixture was cooled down to 15° C. over 4.5 h and stirred at this temperature for 2 h; then the product was centrifuged (2 loadings) and the cake washed with cold methylethylketone (2×34 kg/loading). The wet product was dried for 1 h at 45° C., then under vacuum (500 mbar to maximum over 5 h) at 45° C. for ~18.5 h and the product sieved at 3 mm and packaged. Yield: 160 kg (95.8%).

Example 5—Recrystallization of Crystalline Form A

Pimavanserin tartrate (3.04 kg) was slurried in ethanol (18.2 L). The slurry was heated at 75° C. until it dissolved. The solution was filtered on a cartridge filter and the filter was rinsed with ethanol (0.9 L). The solution was cooled over 1 h to 55° C. and seeded with crystalline Form A of pimavanserin tartrate (0.02 kg). The suspension was cooled to −10° C. in 3 h and stirred at this temperature for 2 h. The product was centrifuged and the cake was washed with cold ethanol (2×1.5 L). The wet cake was dried at 25-30° C. for 5 days to obtain 2.8 kg of product (yield=92.4%).

It was discovered that the yield of manufacturing scale product was improved when the temperature of the suspension was decreased (e.g., to about 10° C. or less, about 0° C. or less, or about −10° C. or less as in this example). Prior methods used a temperature of about 20° C. with lower yields (about 87%).

Example 6—Recrystallization of Crystalline Form C

A suspension of pimavanserin tartrate (8M) in pre-filtered and degassed methyl ethyl ketone was heated to 60° C. and stirred for 8 h under nitrogen atmosphere. The mixture was cooled to 15° C. over 4.5 h and stirred for 2 h, then the product was centrifuged and the cake washed with cold (15° C.) prefiltered and degassed methyl ethyl ketone. The wet product was dried for 15 h in vacuo at 45° C., discharged, packaged under nitrogen and stocked at 0 to 4° C. By using an oxygen free environment, oxidation of product was prevented and complete conversion to polymorph Form C was observed after 2 hours of stirring at 60° C. Yield 95.1%.

Additional methods for the preparation of pimavanserin, salts and crystalline forms thereof, are found in U.S. Pat. Nos. 7,732,615; 7,795,547; 7,790,899; 7,868,176 and 8,236,960, the entireties of which are hereby incorporated by reference.

Example 7: Phase III Clinical Results in PDP Patients

A six-week, multi-center, randomized, double-blind, placebo-controlled study was conducted in PDP patients. The purpose of the study was to evaluate the safety and efficacy of 40 mg pimavanserin compared to placebo in the treatment of PDP.

A total of 199 patients were enrolled in the study and randomized on a one-to-one basis to receive either 40 mg of pimavanserin or placebo once daily for six weeks, following a two-week screening period including brief psycho-social therapy. Patients also received stable doses of their existing anti-Parkinson's therapy throughout the study.

The trial was conducted on an outpatient basis with visits performed as follows: Screening Visit 1, Day 1 (Baseline), Day 15, Day 29 and Day 43 with a follow-up visit (Day 71) 4 weeks after the last regular study visit for those subjects who did not continue into an open-label extension protocol. At the screening visit, a trained member of the site staff worked with the patient's caregiver to devise a structured plan of social interaction for the patient and caregiver to follow at home. This brief non-pharmacologic psychosocial counseling was intended to help the patient and caregiver to manage the symptoms and provide standard of care prior to the blinded investigational treatment phase. Following the screening visit, patients received two follow-up phone calls (~3- and 7-days from the screening visit) to review the plan and evaluate progress. Only those patients who met entry criteria at baseline were randomized to receive 40 mg pimavanserin or matching placebo for the 6-week treatment period.

Each subject participated in the study during a screening period lasting up to 2 weeks, a 6-week investigational treatment period, and a 4-week follow-up period, for those subjects who do not continue onto an open-label safety extension protocol. The maximum duration of the study for each subject was approximately 12 weeks. Pimavanserin was administered in tablet form, once daily by mouth in 40 mg doses (2 tablets of 20 mg). Placebo was administered with visibly matching tablets, using the same route and regimen. The safety of subjects was assessed by monitoring adverse events, physical examinations, vital signs, clinical laboratory tests (hematology, clinical chemistry, and urinalysis), and electrocardiograms.

Brief Psycho-Social Therapy Period for PD Patients (BPST-PD)

The study included a modification to the screening period such that patients received up to 2 weeks of brief psycho-social therapy (BPST) designed as per current supportive care guidelines and modified for PD to aid the patient and caregiver in the management of psychotic symptoms prior to randomization. Patients who responded sufficiently to this non-pharmacologic social interaction therapy (i.e., who no longer meet study entry criteria), were not randomized into the blinded treatment period. Patients who did not materially improve during this phase had the option of entering the treatment period early.

BPST-PD was used in this trial to reduce placebo responses in PDP patients. BPST was developed for use in clinical trials of Alzheimer's patients with behavioral disorders where placebo response rates often exceed 40%. It has been proposed that these high rates of placebo response result from a combination of Hawthorne effect and spontaneous remission. Hence many people may show improvement without active medication and efficacy of pharmacologic treatments may be masked in therapeutic trials. The utility of BPST for the treatment of agitation in Alzheimer's disease (the CALM-AD trial) was recently reported in American Journal of Geriatric Psychiatry (Ballard et al., 2009). In the CALM-AD study, BPST treatment achieved a 6-point reduction on the Cohen-Mansfield Agitation Inventory. In addition, significant reductions in agitation have been reported in 2 other randomized controlled trials (Cohen-Mansfield et al., 1997 and Cohen-Mansfield et al., 2007).

BPST-PD non-pharmacologic therapy was administered over the 2-week screening period by a trained site staff member working with the PD patient's principle caregiver to train and implement the therapy at home. The treatment is simple and clinically applicable, comprising a series of social interactions between the caregiver and patient based on a plan designed specifically for them. The trained site staff member interacts with the caregiver at the screening visit to explain the BPST-PD and mutually develop the social interaction plan for the patient/carer dyad. The site staff member then followed up by phone or in person at 3-7 day intervals during the 2-week screening period to review the plan and monitor implementation.

Exemplary 2-Week Screening Period Protocol

BPST-PD entails daily 10-30 minute semi-structured interactions between the patient and caregiver. These interactions may be incorporated into time already dedicated to caretaking such as while bathing, feeding and otherwise caring for the patient. The caregiver will require training and assistance from site staff in developing and implementing an individually-designed interaction strategy for the patient involved. There will be a total of 4 visits (2 at the clinic and 2 by phone), as follows, between the site staff and the caregiver during the 2-week screening period leading up to baseline/randomization. The purpose of each visit is summarized below:

Screening Visit 1 (SV1):

BPST-PD training of the caregiver occurs in the clinic at this first study visit. This session is specifically designed to help understand each patient and design a plan of interaction. This session will last approximately 30 minutes. The following suggested script (indented paragraphs below) is intended to guide site staff in the initial caregiver interview such that an individualized intervention plan for the patient and caregiver can be devised:

The goals of this BPST session are:
(i) to help you, the caregiver, to complete an assessment of the person with PDP. We will be interested in details about the patient's past history, personal experiences, and current behaviors.
(ii) based on this assessment, we will work together to devise an intervention plan specific for the patient and you.

Overview: This 30-minute training session will be followed by 3 additional follow up visits (conducted either by phone or in person) to support you during implementation of the intervention plan. The intervention entails daily one-to-one social interactions between you and the patient during the 2-week screening period. These interactions may be as simple as a conversation or other shared activity selected from the list below. It is important that the time spent with the patient is dedicated and undisturbed and therefore, to the extent possible, any radio and television should be turned off and any other interruptions minimized while the social interaction takes place. The activity should continue for at least 10-30 minutes and for as long as the patient wishes to continue participation. The intervention should be personalized to the patient based upon the assessment of "background features".

Initiation of one to one communication: To initiate the interaction a statement such as "I thought it would be nice to have a chat or do something together. Would you like that?" should be made. If the patient chooses to engage in a chat, a conversation could be initiated using a prompt regarding the person's past life. Examples might be: Do you remember when we . . . ? Didn't we . . . ?." Or similar prompts related to past hobbies, previous places of residence or other topics relevant to the patient. The use of a photo album or other appropriate materials to prompt the discussion may be useful.

If a person declines the interaction his/her wishes should be respected. A further attempt to initiate the activity could be made at a later time. The offer of a cup of tea or coffee may act to normalize the social interaction and increase the motivation of the person to participate.

Activities for one to one interactions: The nature of the activities undertaken will depend on the ability of the person with PDP—see below (a to c).

The first activities (a & b) require a more active involvement from the patient compared to the latter activity (c). We will help you will select the most appropriate interactions to try with the person. The selection will depend on the person's impairment and personal likes and dislikes. It may be that more than one activity is selected. If the caregiver has ideas for other structured activities that the patient might enjoy, these may be considered.

Activities:
(a) Manual and mental activities, such as making/doing a simple jigsaw or crossword puzzle. Remind the caregiver that they can function as the patient's hands if Parkinson's symptoms are too severe.
(b) Physical based activity such as taking a walk, gardening, setting tables, washing up. This may also help the person feel more included and help them to have fun and enjoy the activity.
(c) Reading to the person from a favorite book, magazine, or newspaper.

A "box of activities" (including games, photographs, favorite books and music, etc.) could be prepared to help you.

Different Topics of Conversation or Activities:

As the shared activity is intended to take place daily over the intervention period, it will probably be necessary to have some variations for the conversation or activity as it may otherwise become boring or repetitive. As far as possible, however, the "variations" should follow the same themes. It is important to keep the therapy simple and focused or there will be a significant detrimental impact on compliance.

Examples may be:

If the interaction is a conversation about vacations, photographs and other reminiscence objects could be drawn together related to several different vacations, enabling the conversation to focus on different vacations on different days.

If the selected activity is a jigsaw, depending on the complexity of the jigsaw—several different puzzles could be used over the two week period. In the event that the jigsaw links to particular episodes in the patient's life, reminiscence objects or conversation prompts could be identified, as appropriate.

Shall we go through the 'Assessment Worksheet' so that we can determine which of these activities would be most appropriate for the patient? [Now complete Assessment Sheet below]

[END OF SCRIPT]

Assessment Sheet: below is an exemplary assessment sheet that may be used as described above:

---

ASSESSMENT SHEET
(To be completed by the trainer during the initial training session)

---

Please provide details about the relevant material under each of these headings. The goal is to focus on things that: 1) May be important with respect to psychosis and related behaviors, and 2) Will help refine the social interaction intervention.
Psychological and social factors:

---

Relevant details about the person's history of PD and psychotic symptoms, their coping style, pre-morbid personality, and social situation. The following may be relevant questions:
Is there a specific time of day that the psychotic symptoms occur?
How agitated does the patient become during these episodes?

ASSESSMENT SHEET
(To be completed by the trainer during the initial training session)

What's the patient's personality like? Has the patient's PD and/or psychosis affected their personality? How?
What does the patient like to do? What are his/her hobbies? Have the patient's interests/hobbies changed because of their PD and/or psychosis?
When the patient is experiencing psychosis, how does the patient cope? How does the caregiver cope?
Are there other family members or friends that interact with the patient routinely? Do they see the patient during episodes of psychosis? How do they cope?
Are there particular social triggers for the onset of psychotic symptoms? Are there practical things that can be done to prevent the triggers?
Environmental factors:

Relevant details about the person's current living environment and ability to cope with and enjoy this setting. The following may be relevant questions:
Where does the patient live? (House, apartment, with extended family, assisted living, etc . . . )
Is there a particular place where the patient experiences psychotic symptoms (indoors/outdoors, bedroom, living room etc.)
Is there anything about the environment that worsens or improves the patient's condition?
Are there particular environmental triggers for the onset of psychotic symptoms? Are there practical things that can be done to prevent the triggers?
Physical factors:

Relevant details about the person's physical condition. The following may be relevant questions:
Are there particular physical limitations that would impede the patient's ability to interact for the purposes of the BPST?
Are there particular physical symptoms of Parkinson's disease that worsen or trigger psychosis for the patient?

Documentation of Plan: Once selected, the intervention plan should be summarized in writing (about 1-page) and include details of the selected activity(ies) to be carried out daily in the one-to-one interactions between the patient and caregiver. It should also prospectively define the expected time and duration of each interaction period. If more than one conversational topic or activity is to be used, it is very important that they are defined carefully in the therapy plan, where possible defining which day each theme will be used. The caregiver should be given a copy of the plan with a second copy retained by the trainer (site staff). The caregiver should be asked to keep a brief diary of each session.

Screening Visit 2 (SV2):

BPST-PD follow-up phone contact occurs approximately 3-4 days after SV1 and should last approximately 15 minutes. The caregiver is contacted to assess how the implementation is going and to provide supportive suggestions for any identified concerns. It should begin with a review of the diary notes of the caregiver. The aim is to re-emphasize key points of the interaction plan. The general approach should be to start by praising any positives: attempts to undertake any intervention, completed interventions, any positive impact upon the person with dementia that is achieved, any pleasure that the caregiver derived from the intervention and any flexible problem solving that the caregiver used to manage, change, and/or implement the intervention. If the intervention has not been implemented, the reasons for this should be elicited. If the caregiver encountered problems with and was unable to implement the intervention effectively, solutions should be proposed. Examples may be:

Caregiver has not understood the intervention: the approach can be re-explained, and then the caregiver asked to explain it themselves in their own words.

Insufficient time to deliver intervention: the reasons can be explored, the times of the intervention can be modified to ones that are more convenient, strategies for eliciting help to cover other conflicting commitments can be explored; sharing of the intervention between caregivers can be explored.

Failure of engagement: if the patient has been unwilling to take part in the intervention, minor changes to the plan or approach may be helpful. For example, to present the intervention at a time of day or for a duration that may be more acceptable to the patient.

There may be a need to make minor adjustments to the intervention based upon a re-formulation of the behavior and the difficulties with implementing the intervention. This may for example incorporate a slightly different strategy for avoiding a trigger, a change of music or emphasis on a different approach within the selection of activities included within the interaction intervention.

Screening Visit 3 (SV3):

BPST-PD Follow-up phone contact occurs approximately 1 week after SV1 or 3-4 days after SV2 and should last approximately 15 minutes. Activities for this visit should include the same review of the caregiver's diary and activities as in SV2 with continued in-person support of the caregiver. Strategies for managing any challenges and improving engagement with the patient should be discussed, as needed. The trainer will again contact the caregiver to assess how the implementation is going and to provide supportive suggestions for any identified concerns.

Screening Visit 4 (SV4=Baseline Visit):

This visit occurs on site at the conclusion of the screening period (approximately 2 weeks after SV1) and is intended to provide closure of the BPST-PD intervention. The emphasis should be on re-enforcing any positives that have come from the intervention. Explain clearly that that the use of BPST may now be discontinued. Explain that a different member of the study team will evaluate the patient to determine if they meet the criteria necessary for moving on to the pharmacological aspect of the study and that the caregiver will be informed of the outcome. Should the patient continue into the active treatment phase, the caregiver's continued support and knowledge of the patient will be important.

The use of BPST-PD may reveal patients who benefit from psycho-social therapy alone, and thereby reduce placebo response in the investigational treatment phase of the clinical study by pulling that response forward of baseline measures. The use of BPST-PD limits randomization only to those patients for whom pharmacologic treatment is appropriate. It may have the added advantage of encouraging investigators who may be reluctant to enroll their more severe patients (i.e., those in need of urgent non-placebo intervention) by offering the patient and caregiver non-pharmacologic psycho-social therapy to help manage symptoms through at least the 2-week treatment period. For those patients who respond to this supportive care, benefit may extend beyond the screening period.

Clinical Study Inclusion Criteria:

i. Male or female of 40 years of age or older with a clinical diagnosis of idiopathic Parkinson's disease with a minimum duration of 1 year, defined as the presence of at least three of the following cardinal features, in the absence of alternative explanations or atypical features: rest tremor, rigidity, bradykinesia and/or akinesia, postural and gait abnormalities.

ii. Female subjects must be of non-childbearing potential (defined as either surgically sterilized or at least 1 year post-menopausal) or must agree to use a clinically acceptable method of contraception (such as intrauterine device (IUD), diaphragm, or oral, injectable (e.g. Depo-Provera) or implantable contraception (e.g. Norplant System), for at least one month prior to randomization, during the study, and one month following completion of the study.

iii. Subjects must have psychotic symptoms that developed after the diagnosis of Parkinson's disease was established. These symptoms must include visual hallucinations and/or auditory hallucinations, and/or delusions.

iv. Psychotic symptoms must have been present for at least one month and the subject must have actively experienced psychotic symptoms each week during the month prior to the Screening visit.

v. Symptoms severe enough to warrant treatment with an antipsychotic agent; documented at screening by items A and B of the NPI, and defined as a score of 4 or greater on either the Hallucinations (Frequency×Severity) or Delusions (Frequency×Severity) scales OR a total combined score of 6 or greater.

vi. At the baseline visit, subject must have a SAPS Hallucinations or Delusions global item (H7 or D13) score ≥3 AND a score ≥3 on at least one other non-global item using the modified 9-item SAPS Hallucinations and Delusions domains.

vii. Subject must have clear sensorium at study entry (i.e., oriented to time, person, and place).

viii. Subjects that are on anti-Parkinson's medication must be on a stable regimen/dose for 1 month prior to Day 1 (Baseline) and during the trial.

ix. Subject that has received stereotaxic surgery for subthalamic nucleus deep brain stimulation must be at least 6 months post surgery and the stimulator settings must have been stable for at least 1 month prior to Day 1 (Baseline) and must remain stable during the trial.

x. The subject is willing and able to provide consent.

xi. Caregiver is willing and able to provide consent and agrees to accompany the subject to all visits.

xii. Subject and caregiver are willing and able to adequately communicate in English for the purposes of the primary endpoint assessments by the MedAvante remote raters.

Primary Clinical Endpoint:

The combined score for the modified 9-item hallucinations and delusions domains of the Scale for the Assessment of Positive Symptoms (SAPS-PD). The nine items from the hallucinations and delusions domain of the SAPS scale have been shown to be particularly relevant to the expression of psychotic symptoms in patients with Parkinson's disease and have high inter-rater reliability for assessment of severity.

Key Secondary Endpoint:

Parts II-III of the Unified Parkinson's Disease Rating Scale (UPDRS), which measures motor function. The objective of this secondary endpoint was to demonstrate that pimavanserin could achieve its antipsychotic effects without worsening motor function as compared placebo in PDP patients.

Other Secondary Endpoints:

Changes in the Clinical Global Impression Scale (CGI) with emphasis on severity (CGI-S) and improvement (CGI-I) of psychosis.

Exploratory Endpoints:

the Caregiver Burden Scale, and Scales for Outcomes in Parkinson's Disease-Sleep scale (SCOPA-Sleep).

Summary of Results:

Pimavanserin met the primary endpoint by demonstrating highly significant antipsychotic efficacy as measured using the 9-item SAPS-PD scale (p=0.001).

These results were further supported by a highly significant improvement in the secondary efficacy measure, the CGI-I scale (p=0.001).

Pimavanserin met the key secondary endpoint for motoric tolerability as measured using Parts II and III of the UPDRS. Pimavanserin conferred antipsychotic activity while maintaining motor control.

Clinical benefits were observed in all exploratory efficacy measures with significant improvements in nighttime sleep, daytime wakefulness, and caregiver burden.

Pimavanserin was safe and well-tolerated in the trial.

Primary Endpoint Results:

SAPS-PD assessments were performed by blinded, independent centralized raters. The pimavanserin arm of the study demonstrated a robust 5.79 point improvement in psychosis at day 43 compared to a 2.73 point improvement for placebo, representing a highly significant and clinically meaningful treatment difference of 3.06 points on SAPS-PD (p=0.001).

|         | Baseline Mean | | Mean Change at Day 43 | | |
|---------|---------|---------------|---------|-------------|---------|
|         | Placebo | Pimavanserin  | Placebo | Pimavanserin | P-value |
|         | (n = 90) | (n = 95) | | | |
| SAPS-PD | 14.73   | 15.88         | −2.73   | −5.79       | 0.001   |

Note:
mixed model repeated measures (MMRM) method was applied in primary analysis of the intent-to-treat (ITT) population. The significance test was based on least-square mean change from baseline for each arm using a 2-sided beta = 0.05.

Key Secondary Endpoint Results:

A pre-specified, non-inferiority analysis was used to compare the mean change from baseline to day 43 for pimavanserin versus placebo using a two-sided 95 percent confidence interval (CI) for the treatment difference. Moteric improvements were seen in both the pimavanserin and placebo arms and the CI associated with the treatment difference did not exceed a pre-specified margin of 5 points for clinically relevant change, confirming that pimavanserin met this key secondary endpoint and did not worsen motor function in PDP patients. Both the pimavanserin and placebo arms showed improvements in combined UPDRS II & III scores (−1.69 for placebo, −1.40 for pimavanserin).

Sleep Improvements:

the SCOPA-sleep scale was used to evaluate nighttime sleep and daytime wakefulness in Parkinson's patients. Pimavanserin demonstrated significant improvements on both nighttime sleep (p=0.045) and daytime wakefulness (p=0.012) on SCOPA.

Caregiver Burden:

the Caregiver Burden Scale was completed by the caregiver to provide a quantitative assessment of burden associated with the patient's functional/behavioral impairments, the circumstances of at-home care, as well as the caregiver's health, social life and interpersonal relations. Pimavanserin demonstrated a highly significant improvement on the Caregiver Burden Scale (p=0.002).

Safety and Tolerability Profile:

pimavanserin was safe and well tolerated in this trial. The most common adverse events were urinary tract infection (11.7% placebo vs. 13.5% pimavanserin) and falls (8.5% placebo vs. 10.6% pimavanserin). The only serious adverse events that occurred in more than one patient were urinary tract infection (1 placebo vs. 3 pimavanserin) and psychotic disorder (zero placebo vs. 2 pimavanserin). Only 5 other adverse events occurred with an incidence greater than or equal to 5% in either arm (peripheral edema, hallucination, confused state, nausea and headache). Adverse events were generally characterized as mild to moderate in nature. Ninety percent of the patients who completed the clinical phase of this trial elected to roll over into the ongoing open-label safety extension study. Patients were only eligible to participate in the extension study if the treating investigator also deemed them to be likely to benefit from continued treatment with pimavanserin.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for reducing caregiver burden during the treatment of Parkinson's disease psychosis patients comprising administering pimavanserin or a pharmaceutically acceptable salt thereof to a Parkinson's disease psychosis patient, wherein the reduction in caregiver burden is measured on the Caregiver Burden Scale.

2. The method of claim 1, wherein the Caregiver Burden Scale is completed by the patent's attending caregiver.

3. The method of claim 1, wherein the Caregiver Burden Scale is completed by a self-administered 22-item questionnaire.

4. The method of claim 1, wherein pimavanserin tartrate salt is administered to the Parkinson's disease psychosis patient.

5. The method of claim 1, wherein pimavanserin or pharmaceutically acceptable salt is administered orally.

6. The method of claim 1, wherein pimavanserin or pharmaceutically acceptable salt, is administered to the patient in a daily dose of about 40 mg.

* * * * *